(12) United States Patent
Kim et al.

(10) Patent No.: US 8,679,768 B2
(45) Date of Patent: Mar. 25, 2014

(54) DIAGNOSIS OF ALZHEIMER'S DISEASE USING Aβ22(PE)-42 PEPTIDE

(71) Applicant: Korea Center for Disease Control and Prevention, Cheongwon-gun (KR)

(72) Inventors: Young-Youl Kim, Chungcheongbuk-do (KR); Seungwoo Kim, Chungcheongbuk-do (KR); Hyo-Soon Cheon, Chungcheongnam-do (KR); Sang Ick Park, Daejeon (KR)

(73) Assignee: Korea Center for Disease Control and Prevention (KR)

( * ) Notice: Subject to any disclaimer, the term of this patent is extended or adjusted under 35 U.S.C. 154(b) by 0 days.

(21) Appl. No.: 13/645,741

(22) Filed: Oct. 5, 2012

(65) Prior Publication Data
US 2013/0089877 A1   Apr. 11, 2013

(30) Foreign Application Priority Data
Oct. 7, 2011   (KR) .................. 10-2011-0102611

(51) Int. Cl.
| | | |
|---|---|---|
| *G01N 33/533* | (2006.01) | |
| *G01N 33/534* | (2006.01) | |
| *G01N 33/535* | (2006.01) | |
| *G01N 33/536* | (2006.01) | |
| *G01N 33/539* | (2006.01) | |

(52) U.S. Cl.
USPC ............ 435/7.1; 435/7.94; 436/539; 436/542

(58) Field of Classification Search
None
See application file for complete search history.

(56) References Cited

U.S. PATENT DOCUMENTS

2011/0117100 A1* 5/2011 Britschgi et al. ........... 424/139.1
2011/0287005 A1  11/2011 Hillen et al.

FOREIGN PATENT DOCUMENTS

WO   2010/006720 A1   1/2010

OTHER PUBLICATIONS

Marcello A et al. (2011) Reduced levels of IgM autoantibodies against N-truncated pyroglutamate Abeta in plasma of patients with Alzheimer's disease. Neurobiol. Aging, 32:1379-1387.*
Andrij Baumketner and Joan-Emma Shea, Folidng Landscapes of the Alzheimer Amyloid-B(12-28) Peptide, J. Mol. Biol. (2006) 362, 567-579.

* cited by examiner

*Primary Examiner* — Kimberly A Ballard
(74) *Attorney, Agent, or Firm* — Lando & Anastasi LLP

(57) ABSTRACT

The present inventors screened peptides having a specific sequence specifically binding to amyloid-beta antibody and accordingly confirmed that Aβ22(pE)-42 peptide showed higher reactivity to amyloid-beta antibody in serum of Alzheimer's disease patients. Therefore, the said Aβ22(pE)-42 peptide can be used as an active ingredient for the kit for diagnosing dementia and thus it can be said that the peptide can be effectively used for the diagnosis of dementia whose early diagnosis is hardly possible.

15 Claims, 2 Drawing Sheets

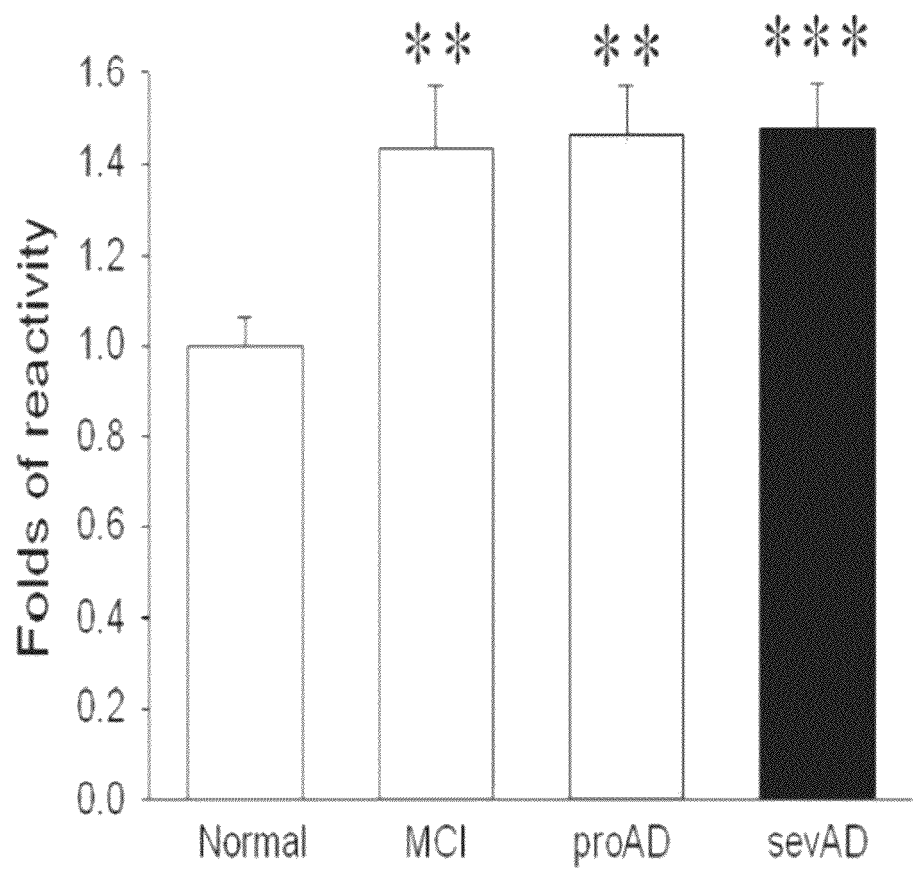

SEQUENCE LISTING

<160> NUMBER OF SEQ ID NOS: 1

<210> SEQ ID NO 1
<211> LENGTH: 21
<212> TYPE: PRT

```
<213> ORGANISM: Homo sapiens

<400> SEQUENCE: 1

Glu Asp Val Gly Ser Asn Lys Gly Ala Ile Ile Gly Leu Met Val Gly
1               5                   10                  15

Gly Val Val Ile Ala
            20
```

DIAGNOSIS OF ALZHEIMER'S DISEASE USING Aβ22(PE)-42 PEPTIDE

The novel Aβ22(pE)-42 peptide that binds to amyloid-beta antibody specifically in blood and pharmaceutical composition for the diagnosis of dementia disease containing the same as an active ingredient

RELATED APPLICATIONS

This application claims priority to Korean Patent Application No. 1020110102611, filed on Oct. 7, 2011, the entire content of which is hereby incorporated herein in its entirety.

BACKGROUND OF THE INVENTION

1. Field of the Invention

The present invention relates to a kit for diagnosis of dementia comprising the novel Aβ22(pE)-42 peptide binding specifically to amyloid-beta antibody in blood as an active ingredient

2. Description of the Related Art

Population aging in Korea and in most of other countries increases interest in senile diseases and accordingly studies have been actively undergoing about senile diseases. Alzheimer's disease is a kind of degenerative diseases and one of the most representative dementia related diseases, which puts heavy mental and physical burden on the shoulder of not only patient himself but also his family. Alzheimer's disease is found in 10% of people at the age of 65~74, 19% of people at the age of 75~84, and 47% of people at the age of 85 and up. Incidence rate of the disease rises every year, which becomes a serious social problem.

None of the prevention method for Alzheimer's disease or the method for early diagnosis has been known so far. Diagnosis of the disease has depended on doctor's clinical opinion and neuropsychological test, indicating only after the disease progresses far, diagnosis can be made, which makes the treatment difficult. Any effective therapeutic agent has not been developed, yet. Compositions for alleviating symptoms are just used.

The most acceptable theory to understand the mechanism of Alzheimer's disease now is "amyloid hypothesis". That is, amyloid-beta existed in patients or plaque generated by amyloid-beta accumulation induces continuous apoptosis of neurons, resulting in the suppression of neuronal transmission and damages in recognition, leading to the outbreak of Alzheimer's disease. Senile plaque and neurofibrillary tangles are observed in the brains of expired patients due to Alzheimer's disease, which are major pathological characteristics of Alzheimer's disease. Particularly, senile plaque is formed by the accumulation of protein and dead cells in outer cell whose major component is a peptide called amyloid-beta (Aβ) (Hardy, J. et al, Nat Neurosci. 1:355-358, 1998). Gradual damage in recognition, which is the major characteristics of Alzheimer's disease, is believed to be caused by abnormal accumulation of amyloid-beta that is produced by proteolysis of amyloid precursor protein (referred as "APP" hereinafter). The precursor APP is decomposed by β-secretase (BSCE) and γ-secretase to generate amyloid-beta (Craven, R., Nat Rev. Neurosci. 2: 533, 2001; David, H. S. et al., Nat Rev. Neurosci. 2: 595-598, 2001; Yankner, B. A., Neuron 16: 921-932, 1996; Selkoe, D. J., Nature 399: A23-A31, 1999). Development of diagnosis indexes for Alzheimer's disease from blood is actively undergoing. Recently, amyloid protein (amyloid-beta, Aβ42, and Aβ40) known as a key player in Alzheimer's disease development is used as standard for the diagnosis of Alzheimer's disease.

In animal models having Alzheimer's disease, the levels of Aβ42 and Aβ40 in serum and cerebrospinal fluid are increased in proportion to aging. Once cognitive impairment starts, the levels of those proteins are decreased. Thus, taking the amyloid protein level in serum as a standard index for the diagnosis of Alzheimer's disease is under controversy. It has been known that amyloid antibody is observed in the brain, blood, and cerebrospinal fluid of both normal healthy people and Alzheimer's disease patients, but the amount or characteristics of amyloid antibody have not been explained, yet.

The method for early diagnosis of Alzheimer's disease and the prevention method thereof have recently been focused on measuring amyloid-beta protein in body by using amyloid-beta antibody. In this method, it is very important to identify amyloid-beta antigen having a specific arrangement binding specifically to the antibody growing specifically in the blood of Alzheimer's disease patients, unlike in normal people.

Therefore, the present inventors screened peptides having specific patterns that bind specifically to amyloid-beta antibody and then confirmed that Aβ22(pE)-42 peptide had comparatively high reactivity against amyloid-beta in serum of Alzheimer's disease patients, compared with in normal people. Accordingly, the present inventors completed this invention by confirming that the said Aβ22(pE)-42 peptide can be used as an active ingredient for the diagnostic kit of dementia and for the diagnosis of dementia whose early diagnosis is very difficult so far.

SUMMARY OF THE INVENTION

It is an object of the present invention to provide a method for diagnosis of dementia using the novel Aβ22(pE)-42 peptide binding specifically to amyloid-beta antibody in blood.

To achieve the above object, the present invention provides a kit for diagnosis of dementia comprising the Aβ22(pE)-42 peptide represented by SEQ. ID. NO: 1 as an active ingredient.

The present invention also provides a method for diagnosis of dementia comprising the following steps:

1) treating blood taken from a test subject on the solid board attached with the Aβ22(pE)-42 peptide represented by SEQ. ID. NO: 1, followed by washing thereof; and 2) diagnosing the subject with dementia or high risk of dementia when the binding intensity of amyloid-beta antibody on the solid board is significantly higher than that of normal people.

The present invention further provides a method for diagnosis of dementia comprising the following steps:

1) treating blood taken from a test subject on the solid board, followed by washing thereof;

2) treating the Aβ22(pE)-42 peptide represented by SEQ. ID. NO: 1 on the solid board, followed by washing thereof; and 3) diagnosing the subject with dementia or high risk of dementia when the binding intensity of the Aβ22(pE)-42 peptide represented by SEQ. ID. NO: 1 on the solid board is significantly higher than that of normal people.

ADVANTAGEOUS EFFECT

As explained hereinbefore, the present inventors screened peptides having a specific sequence specifically binding to amyloid-beta antibody and accordingly confirmed that Aβ22(pE)-42 peptide showed higher reactivity to amyloid-beta antibody in serum of mild cognitive impairment patient.

Therefore, the said Aβ22(pE)-42 peptide can be effectively used as an active ingredient for the kit for diagnosis of dementia, in other words it can be effectively used for the diagnosis of dementia whose early diagnosis has been hardly made.

BRIEF DESCRIPTION OF THE DRAWINGS

The application of the preferred embodiments of the present invention is best understood with reference to the accompanying drawings, wherein:

FIG. 2 is a graph illustrating the result of quantitative analysis with the said FIG. 1.

DESCRIPTION OF THE PREFERRED EMBODIMENTS

Figure 1:
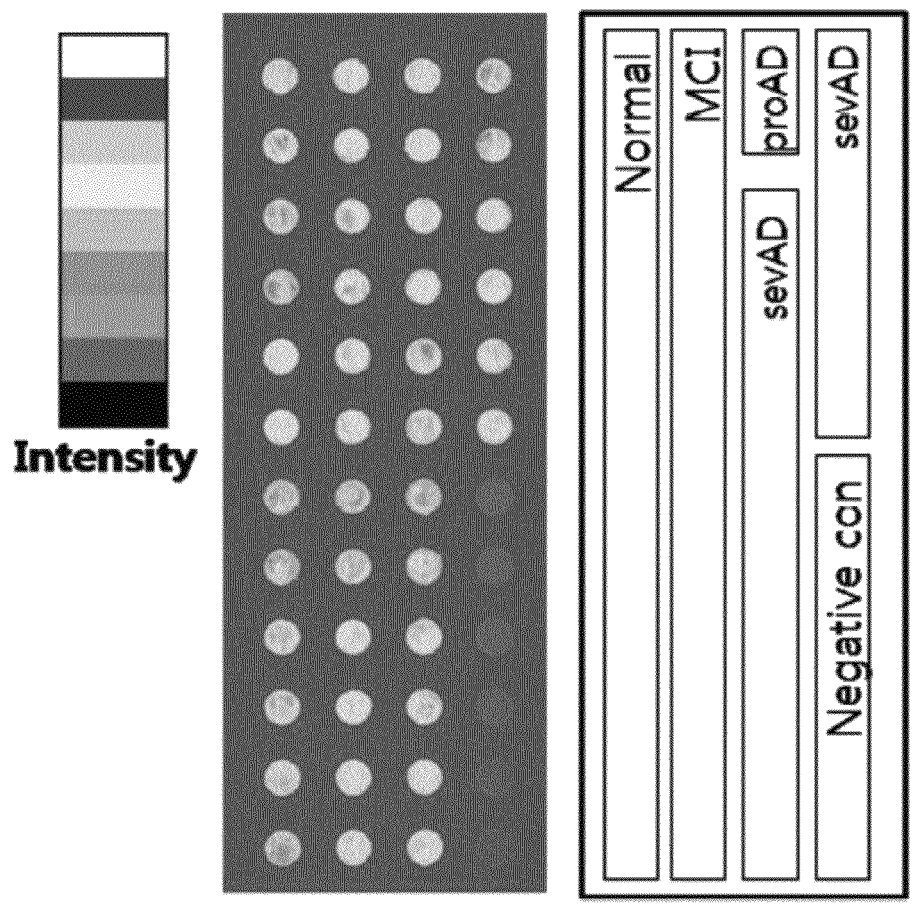
FIG. 1 is a diagram illustrating the immune reactivity of Aβ22(pE)-42 peptide to amyloid-beta antibody:
Normal: normal people;
MCI: mild cognitive impairment;
sevAD: severe Alzheimer's disease;
proAD: probable Alzheimer's disease; and
Negative con: negative control.

Hereinafter, the present invention is described in detail.

The present invention provides a kit for diagnosis of dementia comprising the Aβ22(pE)-42 peptide represented by SEQ. ID. NO: 1 as an active ingredient.

The said peptide can be the one binding to amyloid-beta antibody, but not always limited thereto.

The said dementia can be selected from the group consisting of mild cognitive impairment (MCI), Alzheimer's disease, and cerebral amyloid angiopathy, but not always limited thereto.

Dementia is defined by declined intellectual functions as severe as causing problems in social life or daily life resulted from decrease of cognitive functions in a variety of fields including memory, language, judgment, etc, which is acquired by structural lesion in the brain. For example, mild cognitive impairment, Alzheimer's disease, and cerebral amyloid angiopathy are included in the criteria of dementia. The generation and accumulation of amyloid might be a reason of the said disease, suggesting that the peptide of the present invention can be applied for diagnosis of such disease.

The peptide herein can be conjugated with chromogenic enzyme, chromogenic material or fluorescent molecule. The chromogenic enzyme herein is HRP (horseradish peroxidase) or alkaline phosphatase. The chromogenic material can be colloid gold, and the fluorescent molecule in this invention can be selected from the group consisting of poly L-lysine-flourescein isothiocynate (FITC), rhodamine-B-isothiocyanate (RITC), Cy2, Cy3, and Cy5, but not always limited thereto.

In particular, when secondary antibody-signal molecule complex is used as a detecting tool, the signal molecule can be selected from the group consisting of fluorescent molecule (ex; Cy3, CY5, FITC, GFP (green fluorescent protein), RFP (red fluorescent protein), and Texas Red), luminescent material, radio isotope, and such enzymes as HRP (horse radish peroxidase), alkaline phosphatase, β-galactosidase, and luciferase, etc, but not always limited thereto.

The kit for diagnosis of dementia of the present invention makes the diagnosis of dementia possible by analyzing quantitatively or qualitatively the binding reactions such as antigen/antibody binding or protein/ligand binding. The said binding reaction herein can be measured by ELISA, radioimmunoassay (RIA), sandwich assay, western blotting, immunoprecipitation, immunohistochemical staining, immunofluorescence method, enzyme-substrate colorimetry, and antigen/antibody agglutination assay.

The kit is characteristically composed of:
1) reactor coated with the Aβ22(pE)-42 peptide represented by SEQ. ID. NO: 1;
2) secondary antibody conjugate conjugated with chromogenic marker whose color is developed by the reaction with substrate;
3) chromogenic substrate solution for the color development reaction with the marker;
4) washing solution for each reaction step; and
5) stop solution to terminate the enzyme reaction.

The secondary antibody conjugate marker can be selected from the group consisting of HRP (horseradish peroxidase), alkaline phosphatase, colloid gold, fluorescent molecule, and dye, but not always limited thereto.

The chromogenic substrate can be selected from the group consisting of TMB (3,3',5,5'-tetramethyl bezidine), ABTS [2,2'-azino-bis(3-ethylbenzothiazoline-6-sulfonic acid)], and OPD (o-phenylenediamine), but not always limited thereto.

To investigate immune reactivity of Aβ22(pE)-42 peptide to amyloid-beta antibody, the present inventors separated antibodies from plasma of normal people (48 people), mild cognitive impairment (MCI) patients (49), probable Alzheimer's disease patients (11), and severe Alzheimer's disease patients (62).

Immuno reactivity was measured by using protein chip. As a result, reactivity of Aβ22(pE)-42 peptide to amyloid-beta antibody was increased in blood obtained from mild cognitive impairment and Alzheimer's disease patients, compared with that in normal people (see FIG. 1). Particularly, reactivity of Aβ22(pE)-42 peptide was specifically increased in mild cognitive impairment patients (143%, $p<0.01$), probable Alzheimer's disease patients (146%, $p<0.01$), and severe Alzheimer's disease patients (148%, $p<0.001$), compared with in normal people (see FIG. 2).

As explained hereinbefore, it was confirmed that immune reactivity of Aβ22(pE)-42 peptide to amyloid-beta antibody was higher in serum of mild cognitive impairment patients. Therefore, the said Aβ22(pE)-42 peptide can be effectively used as an active ingredient for the kit for diagnosis of dementia, in other words it can be effectively used for the diagnosis of dementia whose early diagnosis has been hardly made.

The present invention also provides a method for diagnosis of dementia using Aβ22(pE)-42 peptide, which comprises the following steps:
1) treating blood taken from a test subject on the solid board attached with the Aβ22(pE)-42 peptide represented by SEQ. ID. NO: 1, followed by washing thereof; and
2) diagnosing the subject with dementia or high risk of dementia when the binding intensity of amyloid-beta antibody on the solid board is significantly higher than that of normal people.

The present invention further provides a method for diagnosis of dementia using Aβ22(pE)-42 peptide, which comprises the following steps:
1) treating blood taken from a test subject on the solid board, followed by washing thereof;
2) treating the Aβ22(pE)-42 peptide represented by SEQ. ID. NO: 1 on the solid board, followed by washing thereof; and
3) diagnosing the subject with dementia or high risk of dementia when the binding intensity of the Aβ22(pE)-42 peptide represented by SEQ. ID. NO: 1 on the solid board is significantly higher than that of normal people.

In the above method, the subject of step 1) is a vertevrate including human, and preferably a mammal particularly exemplified by human, apes, cow, pig, rat, rabbit, guinea pig, hamster, dog, and cat, but not always limited thereto.

In the above method, the binding intensity between Aβ22 (pE)-42 peptide and amyloid-beta antibody can be measured by a method selected from the group consisting of Western blotting, enzyme-linked immunosorbent assay (ELISA), immunohistochemical staining, immunoprecipitation, and immunofluorescence assay, but not always limited thereto.

Since it was confirmed that Aβ22(pE)-42 peptide demonstrated higher immune reactivity against amyloid-beta antibody in serum of Alzheimer's disease patients than normal people, the Aβ22(pE)-42 peptide can be effectively used for the diagnosis of dementia.

The present invention also provides a method for the detection of amyloid-beta antibody to provide information useful for the diagnosis of dementia using Aβ22(pE)-42. The method herein is composed of the following steps:

1) treating blood taken from a test subject on the solid board attached with the Aβ22(pE)-42 peptide represented by SEQ. ID. NO: 1, followed by washing thereof; and 2) diagnosing the subject with dementia or high risk of dementia when the binding intensity of amyloid-beta antibody on the solid board is significantly higher than that of normal people.

In addition, the present invention provides a method for detecting amyloid-beta antibody to provide information useful for the diagnosis of dementia using Aβ22(pE)-42 peptide. This method is composed of the following steps:

1) treating blood taken from a test subject on the solid board, followed by washing thereof;

2) treating the Aβ22(pE)-42 peptide represented by SEQ. ID. NO: 1 on the solid board, followed by washing thereof; and 3) diagnosing the subject with dementia or high risk of dementia when the binding intensity of the Aβ22(pE)-42 peptide represented by SEQ. ID. NO: 1 on the solid board is significantly higher than that of normal people.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Antigen-Antibody Separation

Plasma was obtained from each of normal people (48 people), mild cognitive impairment patients (MCI, patients), probable Alzheimer's disease patients (11 patients), and severe Alzheimer's disease patients (62 people), which was diluted in dissociation buffer (TBS buffer, 1.5% BSA, 0.2M glycine-acetate, pH 2.5) at the ratio of 1:500, followed by standing at room temperature for 20 minutes. The diluted Plasma was loaded in Amicon Ultra-0.5 ml 10K Ultracel (Millipore, Ireland) filter, followed by centrifugation at 8000 g at room temperature for 20 minutes. The filter was made inside-out and loaded in a new Amicon tube, followed by centrifugation at 1000 g for 2 minutes. At that time, pH was regulated to 7.0 by using 1 M Tris buffer (pH 9.0).

Example 2

Protein Chip Assay

6× His-antibody (Abcam, UK) was diluted in TBS-glycerol buffer (30% glycerol, pH 7.4) at the concentration of 1 μg/ml, which was loaded on protein chip (Proteogen, South Korea) by 1 μl at a time, which stood at 4° C. for overnight or at 37° C. for 3 hours. 6× His-antibody on the chip was eliminated by using 3M paper, followed by washing softly with washing buffer (TBS buffer, 0.1% tween 20) three times at 10 minutes intervals. The remaining washing buffer on the chip was washed out with distilled water by shaking lightly for 10 minutes, followed by centrifugation at 1500 rpm for 3 minutes to eliminate the remaining solution. Blocking buffer (TBS buffer, 0.1% tween20, 3% BSA) was added thereto, followed by reaction with shaking lightly for 1 hour at room temperature. Washing was performed by the same manner as described above. Supernatant was eliminated by centrifugation. Aβ22(pE)-42 peptide (pyrEDVGSNKGAIIGLMVG-GVVIA, SEQ. ID. NO: 1) (Peptide 2.0 Inc, www.peptide2.com) (TBS-glycerol buffer, 3% BSA) was loaded on the chip by 1 μl at a time, which stood at 37° C. for 1 hour. Then, liquid on the chip was eliminated. The antibody separated in Example 1 was diluted with antibody dilution buffer (TBS-glycerol buffer, 3% BSA) at the ratio of 1:4, which was loaded on the chip by 1 μl. Then the chip was stood at 37° C. for 1 hour. One hour later, liquid on the chip was eliminated and the secondary antibody (Anti-human IgG, cy5) diluted in antibody dilution buffer at the ratio of 1:5000 was loaded on the chip by 1 μl. Then the chip was stood at 37° C. for 30 minutes. 30 minutes later, liquid on the chip was eliminated. The result was confirmed by using chip scanner.

Immuno reactivity was measured by using protein chip. As a result, immune reactivity of Aβ22(pE)-42 peptide to amyloid-beta antibody was increased in blood obtained from mild cognitive impairment patients and Alzheimer's disease patients, compared with that in blood of normal people (FIG. 1). Particularly, Aβ22(pE)-42 peptide demonstrated higher immune reactivity to amyloid-beta antibody in blood of mild cognitive impairment patients (143%, p<0.01), probable Alzheimer's disease patients (146%, p<0.01), and severe Alzheimer's disease patients (148%, p<0.001) than that in blood of normal people (FIG. 2).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for diagnosis of mild cognitive impairment (MCI) or Alzheimer's disease, the method comprising the following steps:
   1) contacting blood, plasma, or serum taken from a test subject with a solid board to which the Aβ22(pE)-42 peptide having the sequence of SEQ ID NO: 1 is attached, followed by washing of the solid board; and
   2) diagnosing the subject with MCI or Alzheimer's disease or with high risk of MCI or Alzheimer's disease when the binding of amyloid-beta antibody from the blood, plasma or serum to the Aβ22(pE)-42 peptide on the solid board is significantly higher than that of normal people.

2. The method of claim 1, wherein the binding of the amyloid-beta antibody is assessed using a secondary antibody as a detecting tool, wherein said secondary antibody is optionally conjugated to a chromogenic enzyme, a chromogenic material, or a fluorescent molecule.

3. The method of claim 2, wherein the chromogenic enzyme is horseradish peroxidase (HRP) or alkaline phosphatase.

4. The method of claim 2, wherein the chromogenic material is colloid gold.

5. The method of claim 2, wherein the fluorescent molecule is selected from the group consisting of poly L-lysine-flourescein isothiocynate (FITC), rhodamine-B-isothiocyanate (RITC), CY2, CY3, CY5 and GFP.

6. The method of claim 1, wherein the binding of amyloid-beta antibody to the Aβ22(pE)-42 peptide is measured by a method selected from the group consisting of Western blotting, enzyme-linked immunosorbent assay (ELISA), radioimmunoassay (RIA), sandwich assay, immunoprecipitation, enzyme-substrate colorimetry, antigen/antibody agglutination assay, and immunofluorescence assay.

7. The method of claim 1, wherein before said contacting of the blood, plasma, or serum with the solid board, the blood, plasma, or serum is treated by one or more of dilution in dissociation buffer, filtration, centrifugation, and addition of buffer to regulate pH.

8. A method for diagnosis of mild cognitive impairment (MCI) or Alzheimer's disease, the method comprising the following steps:
   1) attaching the Aβ22(pE)-42 peptide having the sequence of SEQ ID NO:1 to a solid board, followed by washing of the solid board;
   2) contacting blood, plasma, or serum taken from a test subject with the solid board, followed by washing of the board; and
   3) diagnosing the subject with MCI or Alzheimer's disease or with high risk of MCI or Alzheimer's disease when the binding of amyloid-beta antibody from the blood, plasma, or serum to the Aβ22(pE)-42 peptide on the solid board is significantly higher than that of normal people.

9. The method of claim 8, wherein the binding of the amyloid-beta antibody is assessed using a secondary antibody as a detecting tool, wherein said secondary antibody is conjugated to a signal molecule.

10. The method of claim 9, wherein said signal molecule is an enzyme, a chromogenic material, a fluorescent molecule, a luminescent molecule, a radioisotope, or a dye.

11. The method of claim 10, wherein the enzyme is horseradish peroxidase (HRP), alkaline phosphatase, β-galactosidase, or luciferase.

12. The method of claim 10, wherein the chromogenic material is colloid gold.

13. The method of claim 10, wherein the fluorescent molecule is poly L-lysine-flourescein isothiocynate (FITC), rhodamine-B-isothiocyanate (RITC), CY2, CY3, CY5, or GFP.

14. The method of claim 8, wherein before said contacting of the blood, plasma, or serum with the solid board, the blood, plasma, or serum is treated by one or more of dilution in dissociation buffer, filtration, centrifugation, and addition of buffer to regulate pH.

15. The method of claim 8, wherein the binding of amyloid-beta antibody to the Aβ22(pE)-42 peptide is measured by a method selected from the group consisting of Western blotting, enzyme-linked immunosorbent assay (ELISA), radioimmunoassay (RIA), sandwich assay, immunoprecipitation, enzyme-substrate colorimetry, antigen/antibody agglutination assay, and immunofluorescence assay.

* * * * *